(12) United States Patent
Foerster et al.

(10) Patent No.: US 7,831,126 B2
(45) Date of Patent: Nov. 9, 2010

(54) WAVEGUIDE CORE AND BIOSENSOR

(75) Inventors: Thilo Foerster, Munich (DE); Christof Strohhoefer, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 12/133,464

(22) Filed: Jun. 5, 2008

(65) Prior Publication Data
US 2009/0202193 A1   Aug. 13, 2009

(30) Foreign Application Priority Data
Feb. 7, 2008   (DE) .................. 10 2008 007 823

(51) Int. Cl.
*G02B 6/00* (2006.01)
*G02B 6/32* (2006.01)
(52) U.S. Cl. .................. 385/142; 385/12; 385/125
(58) Field of Classification Search ............ None
See application file for complete search history.

(56) References Cited

U.S. PATENT DOCUMENTS

| | | | |
|---|---|---|---|
| 5,938,595 A | 8/1999 | Glass et al. | |
| 7,440,110 B2* | 10/2008 | Hjelme et al. ............ | 356/477 |
| 2002/0071625 A1 | 6/2002 | Bartholomew et al. | |
| 2003/0112443 A1 | 6/2003 | Hjelme et al. | |
| 2003/0133639 A1* | 7/2003 | Tao et al. ................ | 385/12 |
| 2003/0138842 A1* | 7/2003 | Seul et al. ............... | 435/7.1 |
| 2005/0094958 A1 | 5/2005 | Dorn et al. | |
| 2006/0147147 A1 | 7/2006 | Zourob et al. | |

FOREIGN PATENT DOCUMENTS

DE   103 50 526 A1   6/2005

OTHER PUBLICATIONS

M. Zourob, A. Simonian, J. Wild, S. Mohr, X. Fan, I. Abdulhalim, and N. J. Goddard, "Optical leaky waveguide biosensors for the detection of organophosphorus pesticides", Analyst (Cambridge, U.K.) 132, 114 (2007). [MEDLINE].*
L. Ding, R. I. Blackwell, J. F. Künzler, and W. H. Knox, "Characterization of Index Changes in Silicone- and Nonsilicone-Based Hydrogel Polymers Induced by Femtosecond Micromachining," (Optical Society of America, 2007), paper CFE5. [online] <url: http://www.opticsinfobase.org/abstract.cfm?URI=CLEO-2007-CFE5>.*
Official communication issued in counterpart German Application No. 10 2008 007 823.9, mailed on Dec. 1, 2008.
Shenkman et al: "The P. Cezanne Project: Innovative Approaches to Continuous Glucose Monitoring", Engineering in Medicine and Biology Society, 29th Annual International Conference of the IEEE, Aug. 1, 2007, pp. 6060-6063.
Official Communication issued in counterpart European Application No. 09000303.9, dated Jun. 26, 2009.
Goddard et al., "Leaky Waveguide Devices As Simple Sensitive Optical Detectors for Use in μTAS Applications", MicroTec 2000, Sep. 25-27, 2000, 6 pages.
Figa et al., "Characterization and Investigation of NLO Properties of Some Selected Electrodeposited Polythiophenes", Journal of the European Optical Society; Apr. 13, 2009; pp. 1-6.

* cited by examiner

*Primary Examiner*—Omar Rojas
(74) *Attorney, Agent, or Firm*—Keating & Bennett, LLP (57) ABSTRACT

A waveguide core made of hydrogel serves as an immobilization matrix having receptor molecules embedded therein.

24 Claims, 7 Drawing Sheets

WAVEGUIDE CORE AND BIOSENSOR

CROSS-REFERENCE TO RELATED APPLICATIONS

This application claims priority from German Patent Application No. 102008007823.9, which was filed on Feb. 7, 2008, and is incorporated herein in its entirety by reference.

TECHNICAL FIELD

The present invention relates to a waveguide core, a waveguide and a biosensor having a waveguide, and in particular to an optical assembly for the measurement of biological, biochemical or chemical parameters.

BACKGROUND

For the realization of metrological jobs on and in biological liquids such as water samples or food, detection methods based on biological receptor molecules may be employed. A metrological job may consist in detecting minimum quantities of an analyte in a solution or sample, which makes tremendous demands on measurement technology. In these methods, receptor molecules ensure the sensitivity and selectivity of the detection (of an analyte or an analyte concentration) by reacting with the analyte and, for example, binding therewith (e.g. via an antibody-antigene interaction). For detecting this reaction, conversion to a processable (optical or electrical) signal is necessitated. This may be effected by means of a physical signal converter—the so-called transducer—for example. A respective biosensor therefore operates on the principle that first a biological or biochemical reaction occurs and then this reaction is converted to a measurable signal.

One major challenge in the development of biosensors consists in coupling the biological receptor molecules and the physical signal converter such that there is maximum and efficient signal carry between the two. This means, for example, that even minimum quantities of the substance to be detected (analyte) (e.g. down to $10^{-13}$ mol/L for tumor markers in the blood serum or 1 . . . 30 mmol/L for glucose concentrations) will result in a measurable signal.

For effecting a reaction between the receptor molecules and the analyte in the sample to be detected, the receptor molecules are first immobilized. For the immobilization of biomolecules, hydrogels and aerogels, for example, may be used in biosensor technology and chromatography. On the other hand, known optical transducers are based on light formed by optical elements (open beam) and, apart from that, on guiding light through an optical waveguide. Light formed by the optical elements may be utilized for transmission measurements, for example, or may be guided along optical trains in the style of microscopy or fluorescence microscopy. The optical waveguide may serve two functions:

(1) transporting light to the location where the analysis takes place or (2) providing an evanescent electromagnetic field on the surface of the waveguide so that the electromagnetic field interacts with the biomolecules found there or the reactions executing there.

The presence of analyte molecules may be evidenced optically as follows:

(i) by interaction with dielectric properties of the molecules on the surface of the waveguide and evidence of a resulting phase shift in an optical interferrometer, (ii) via selective decoupling of certain waveguide modes from the waveguide due to the refractive index of analyte molecules, (iii) via a specific absorption of a molecule (e.g., interaction of an analyte molecule with a receptor molecule may manifest itself in a formation of a specific spectral line), (iv) via a fluorescence of the molecules or the marker fluorophores attached to the molecules, (v) via fluorescence quenching as a result of specific reactions (e.g., a selected fluorescence may be quenched when the receptor molecules interact or bind with the analyte molecules), (vi) via a resonant energy transfer between fluorescent molecules (FRET) and the changes thereof in dependence on the analyte concentration.

The optical waveguide transducers have in common that they either have to in part make do with unguided light and the resulting diffraction and aperture effects in the interaction with the medium to be examined, or that only a small portion of the light (the evanescent field) achieves interaction with the analyte and/or receptor molecules. In order to eliminate the latter problem, above all materials having a very high refractive index (e.g. $Ta_2O_5$, $TiO_2$) are used, of which very thin and well-controlled layers may be fabricated in complex, clean-room-based processes. The thin layers may range below 100 nm or slightly above.

For the aforementioned reasons, the number of receptor molecules capable of taking part in evidencing molecules is strictly limited. Open-beam optical solutions, in spite of being very efficient, suffer from the high space requirements of good beam-forming elements (such as lenses, mirrors, etc.). The use of microlenses provides only little improvement as the microlenses in turn strictly limit the measurable sample volume. Particularly in the field of microfluidic biosensors and biochips in but also in the field of real-time sensors suitable for long-term use, the issues mentioned pose substantial limitations.

SUMMARY

An embodiment may have: a waveguide core made of hydrogel, which serves as an immobilization matrix having receptor molecules embedded therein.

According to another embodiment, a waveguide assembly may have: a waveguide core made of hydrogel, which serves as an immobilization matrix having receptor molecules embedded therein, the waveguide core having an input side; and a fiber-optic cable, wherein the fiber-optic cable protrudes into the input side of the waveguide core or is set upon the input side or is optically coupled to the input side via a lens.

According to another embodiment, a waveguide may have: a waveguide core made of hydrogel, which serves as an immobilization matrix having receptor molecules embedded therein; and a waveguide cladding, the waveguide cladding exhibiting a refractive index smaller than a refractive index of the waveguide core.

According to another embodiment, an optical sensor may have: a waveguide core made of hydrogel, which serves as an immobilization matrix having receptor molecules embedded therein; and a detector for detecting electromagnetic radiation leaving the waveguide core.

According to another embodiment, a method of detecting an analyte in a medium may have the steps of: contacting a waveguide core with the medium, the waveguide core having hydrogel and the hydrogel serving as an immobilization matrix for receptor molecules; detecting electromagnetic radiation leaving the waveguide core; and determining an analyte concentration in the medium from a spectrum or from an intensity of the electromagnetic radiation detected.

The central idea of the present invention consists in not only utilizing a waveguide for feeding and carrying off a light signal but also designing the waveguide as an immobilization matrix for the receptor molecules and using hydrogel as the immobilization matrix. In addition, a biosensor may comprise a waveguide or waveguide core made of hydrogel and means for detecting electromagnetic radiation leaving the waveguide.

Therefore, embodiments of the present invention include the use of hydrogels in the functional combination as an immobilization matrix for biological receptor molecules and at the same time as an optical waveguide or at least a waveguide core. This enables the realization of highly efficient use of light at the location at which the receptor molecules are immobilized. By means of appropriate dimensioning, a maximum number of receptor molecules may take part in evidencing the analyte. The length of the waveguide in the main direction of the wave propagation may be at least five times or three times the height and width of the waveguide, and this relation may hold true for the entire length of the waveguide, for example, so that the waveguide may exhibit an elongated extension. The wave propagation main direction may be the direction in which a maximum, or at least 50%, or at least 70% of the radiation propagates. In the following, the wave propagation main direction is also, for reasons of abbreviation, termed wave propagation direction.

This concept is of particular interest for applications in which no high-performance energy sources are available. One example is implanted biosensors, the reliability of which is based on utilizing the energy quantity (light) available as efficiently as possible. Inefficient energy utilization would not only restrict the lifetime of the energy storage (e.g. a battery), but also result in unnecessary heat production. Moreover, by guiding the light in the immobilization matrix, the interaction zone between the liquid to be analyzed and the biosensor may be expanded virtually without restraint. This may be achieved by using a hydrogel that is transparent to the wavelength used and in addition exhibits a higher refractive index than the refractive index of the medium to be examined or the liquid to be examined (environment) or of surrounding waveguide cladding.

In addition, the biosensor may comprise an optical connection to the exterior (environment)—for example via an optical input, which may comprise (micro) lenses, or via a possibility of connecting a specific laser, an LED, another non-coherent radiation source or any other light source.

Hydrogels typically comprise polymers, the molecules of which are chemically or physically linked to form a three-dimensional network, wherein covalent and ionic bonds may be present, or else entangling the polymer chains may result in a physical stability of the polymers. Built-in hydrophilic polymer components, for example, may serve to make them swell up in water, thereby substantially increasing their volume but not losing their material coherence. Hydrogels may therefore be understood as a polymer network, the pores of which are filled with surrounding liquid. This sees to it that—as long as the refractive index of the polymer has a higher refractive index than the surrounding liquid—there is a difference of the refractive indices of the hydrogel and the surrounding liquid, wherein the hydrogel has the higher refractive index.

Alternatively, the hydrogel may be embedded in a material having a refractive index below the refractive index of the hydrogel filled with the liquid and therefore being capable of acting as waveguide cladding. In this instance, the filled hydrogel represents a waveguide core, which guides the light via a total reflection occurring. Special materials such as fluorinated polymers may be used for the waveguide cladding. However, the waveguide cladding may also comprise an (other) hydrogel as long as the refractive index thereof is less than that of the hydrogel in the waveguide core.

The hydrogel may be disposed in the surrounding liquid in a free-floating manner, for example, and may be rested or suspended at the ends thereof. In this manner, a bulk of the hydrogel between the resting points represents an optical waveguide. The form of the hydrogel waveguide or the waveguide core may be manifold, possible designs being cuboid-shaped or cylindrical, for example.

Spherical, disc- or sickle-shaped designs are also possible. In these designs of the hydrogel, the light may be irradiated tangentially and as close to the edge as possible (e.g. by means of a micromirror) so that the light propagates along the round edge as a result of multiple reflections. If desired, the light may be detected by a detector again in a tangential manner, or else it propagates in the exemplary sphere for an undefined period of time—e.g. until it is "used up" due to fluorescence occurring.

In further embodiments of the waveguide, the hydrogel is disposed in the form of a layer on a thin transparent support, wherein the thin transparent support may comprise silicate glass, for example. In a liquid environment, this arrangement then serves as a waveguide. In further embodiments, coupling light into the waveguide via an open beam or a fiber-optic cable, wherein the fiber-optic cable (optical glass fiber, optical polymer fiber, multi-strand light guide, etc.) may be introduced into the hydrogel, thereby establishing perfect optical contact. Advantageously, the fiber-optic cable is introduced so far into the hydrogel that its end (at which the optical light is coupled into the hydrogel) protrudes beyond the first resting point with which the hydrogel is fixed. In this manner, no light may couple out of the hydrogel waveguide at the resting points.

It is further possible, however, that the light in the waveguide is again captured by a fiber-optic cable on the opposite side in terms of the wave propagation direction. This is, however, optional and reasonable in particular in some assemblies (for measuring absorption, for example), whereas, in other assemblies, such as a fluorescence excitation, capturing the light guided through may be done away with.

In a further embodiment, particular use is made of the scattered or fluorescent light for the detection of an analyte concentration in the medium, wherein a photodetector for analysis is positioned in a manner perpendicular to the wave propagation direction. As a very small portion of the exemplary fluorescent light is guided in the hydrogel, it is advantageous to use an assembly in which the measurement of the fluorescence or the FRET is effected in a manner perpendicular to the optical train of the light in the waveguide.

Embodiments of the present invention also include a method of detecting an analyte in the medium, wherein the method comprises contacting a waveguide with the medium, detecting electromagnetic radiation leaving the waveguide and determining an analyte concentration in the medium from the spectrum or the intensity of the electromagnetic radiation detected. In the inventive method, the waveguide also comprises hydrogel, which simultaneously serves as an immobilization matrix for receptor molecules.

Usually, a waveguide comprises a core and a cladding, wherein the refractive index of the core is higher than the refractive index of the cladding. In embodiments, either the liquid (medium) in which the hydrogel is located serves as the cladding material. This means that the waveguide is not entirely made of hydrogel. In principle, the waveguide may also be made up of a hydrogel serving as the core, and a polymer material, for example, serving as the cladding. Alternatively, the core could be made up of a solid material and the cladding of hydrogel (with immobilized biomolecules or receptor molecules). What is of relevance is the scenario that the core of the waveguide consists of hydrogel having a refractive index n1, and the cladding consists of a hydrogel having a refractive index n2<n1. This serves to maintain all benefits of the assembly.

BRIEF DESCRIPTION OF THE DRAWINGS

Embodiments of the present invention will be detailed subsequently referring to the appended drawings, in which:

FIGS. 2a, b show cross-sectional views of the waveguide with the optical train drawn in;

DETAILED DESCRIPTION

With respect to the following description, it is to be noted that like functional elements or functional elements having the same effect are designated with like reference numerals in the different embodiments and that the descriptions of these functional elements in the different embodiments represented in the following are therefore interchangeable.

Figure 1:
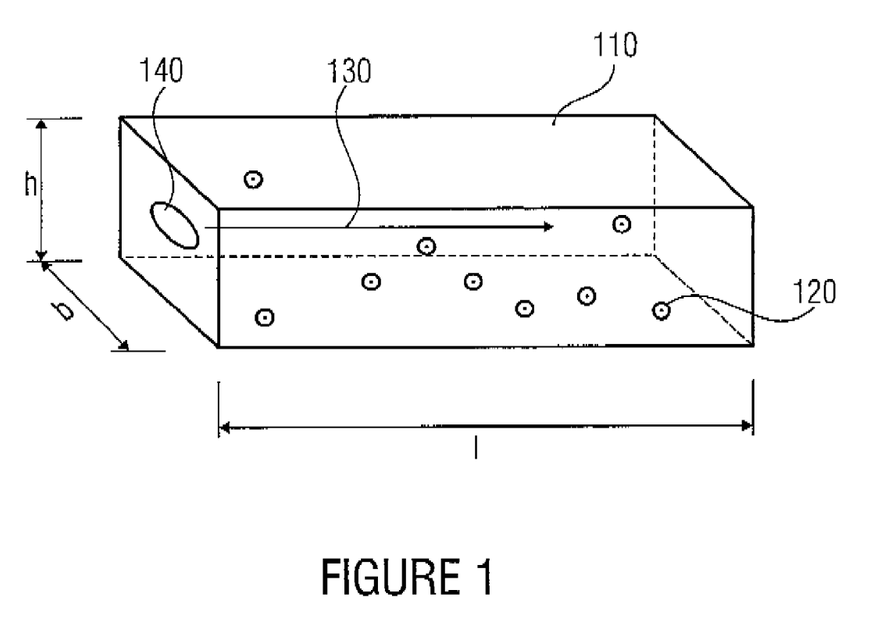
FIG. 1 shows a spatial view of the waveguide according to an embodiment of the present invention.

FIG. 1 shows a spatial view of the waveguide core 110 comprising hydrogel and serving as an immobilization matrix for receptor molecules 120, wherein, for the embodiment shown in FIG. 1, a wave propagation direction 130 (=direction of light guided through the waveguide core) is effected from left to right. The waveguide core 110 may also be a waveguide, and in the following both terms are used parallely. The waveguide 110 exhibits a length 1 and a cross-section in a position perpendicular thereto having a smallest extension h and a largest extension b. The shape of the cross-section is given in the shape of a rectangle or square in FIG. 1, wherein, in further embodiments, the shape of the waveguide 110 may vary. It is, however, of particular advantage when the length of the waveguide 110, measured in the wave propagation direction 130, is considerably larger than the maximum extension of the cross-section. This serves to ensure, for example, that a light signal coupled in on an input side 140 (such as via an open beam or a laser and optional lenses/mirrors) propagates as intensively as possible and across a far distance along the waveguide 110 and therefore may potentially interact with a maximum of receptor molecules 120.

Figure 2A:
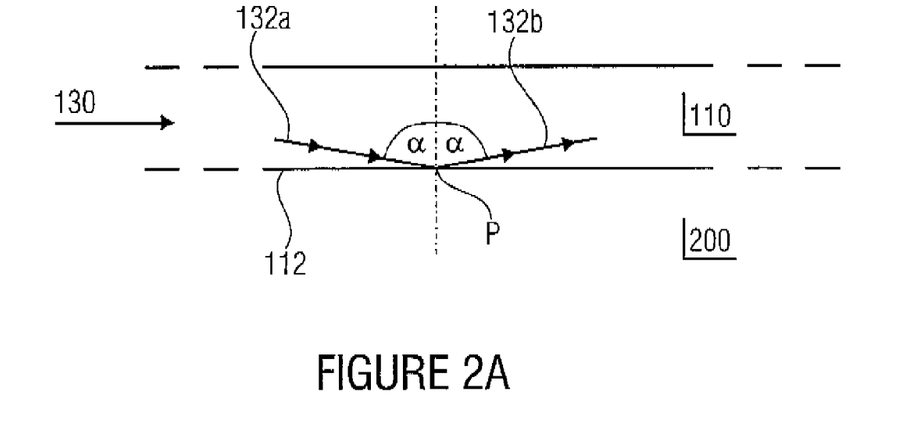
Figure 2B:
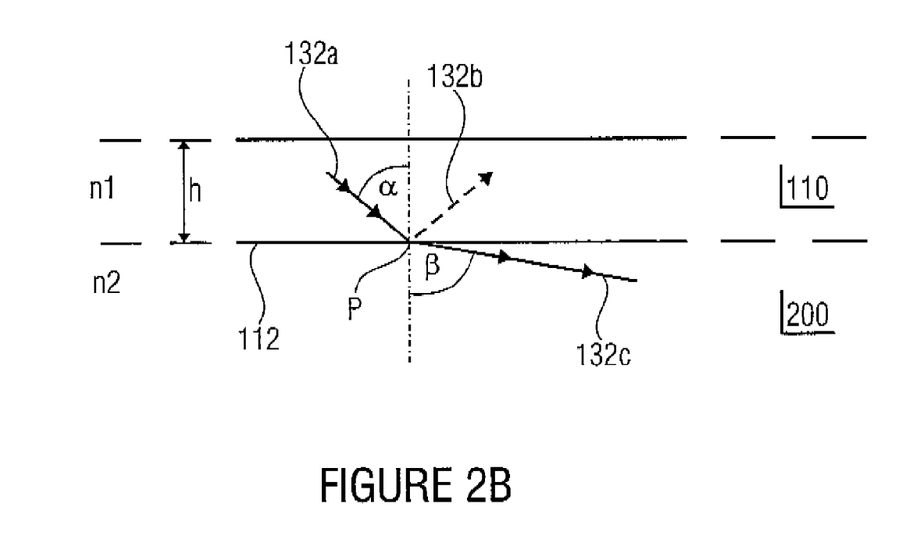

FIGS. 2a and b show cross-sectional views of the waveguide 110 embedded in a medium 200 or in contact with the medium 200. For the waveguide 110 to forward an incident light signal or generally an incident electromagnetic radiation along the wave propagation direction 130, and for the electromagnetic radiation not to leave the guide (by means of refraction), advantageously, the refractive indices are selected such that the refractive index n1 of the waveguide 110 is larger than the refractive index n2 of the medium 200. The result is that a light signal 132a, for example, is incident on an edge 112 of the waveguide 110 at an angle of incidence α (measured to the normal to surface) and is reflected at the edge 112, so that a reflected light signal 132b, again exhibiting an angle of reflection α to the normal to surface, continues to propagate along the waveguide 110. If the refractive index n1 of the waveguide 110 were less than the refractive index n2 of the surrounding medium 200, such a reflection on the edge 112 would be suppressed, and the incident light signal 132a would instead leave the waveguide 110 at the point P. This would, however, be disadvantageous as, as a result of such refractions, the light beam would continuously decrease in intensity, whereby the detection sensitivity would be significantly reduced.

FIG. 2b shows the case that an incident light signal 132a is incident onto a point P at an angle of incidence α being less than a critical angle, so that a reflected output signal 132b is still produced but a refracted proportion 132c leaves the waveguide 110. The total reflection occurs for all angles α being larger than a critical angle, which corresponds to that angle where the refracted light signal 132c would propagate along the edge curve 112. The critical angle is given by the ratio of the two refractive indices, n1, n2. In dependence on the refractive indices of the waveguide 110 and the medium 200, the minimum extension h may now be selected such that a light signal substantially propagating along the propagation direction 130, may only be incident on the edge 112 of the waveguide 110 at an angle that causes total reflection. It is important to choose such a geometry of the waveguide 110 so as to obtain maximum sensitivity of the biosensor, i.e., that only that light may leave the waveguide 110 that is incident, due to fluorescence, for example, on the edge 112 in a manner virtually perpendicular.

Provided that the refractive index of the waveguide 110 is virtually identical to the refractive index of the medium 200, an additional cladding may be used, for example, which is disposed on the waveguide 110 or at a certain distance from the edge 112 of the waveguide 110. The cladding has advantageously a smaller refractive index than the medium 200. This serves to ensure that electromagnetic radiation propagating along and leaving the waveguide 110 is totally reflected on the cladding and is therefore again guided through the waveguide 110 and can interact with potential receptor molecules 120.

The angle of reflection β may be calculated for the waveguide 110 and for the medium by means of the refractive indices n1, n2.

Figure 3A:
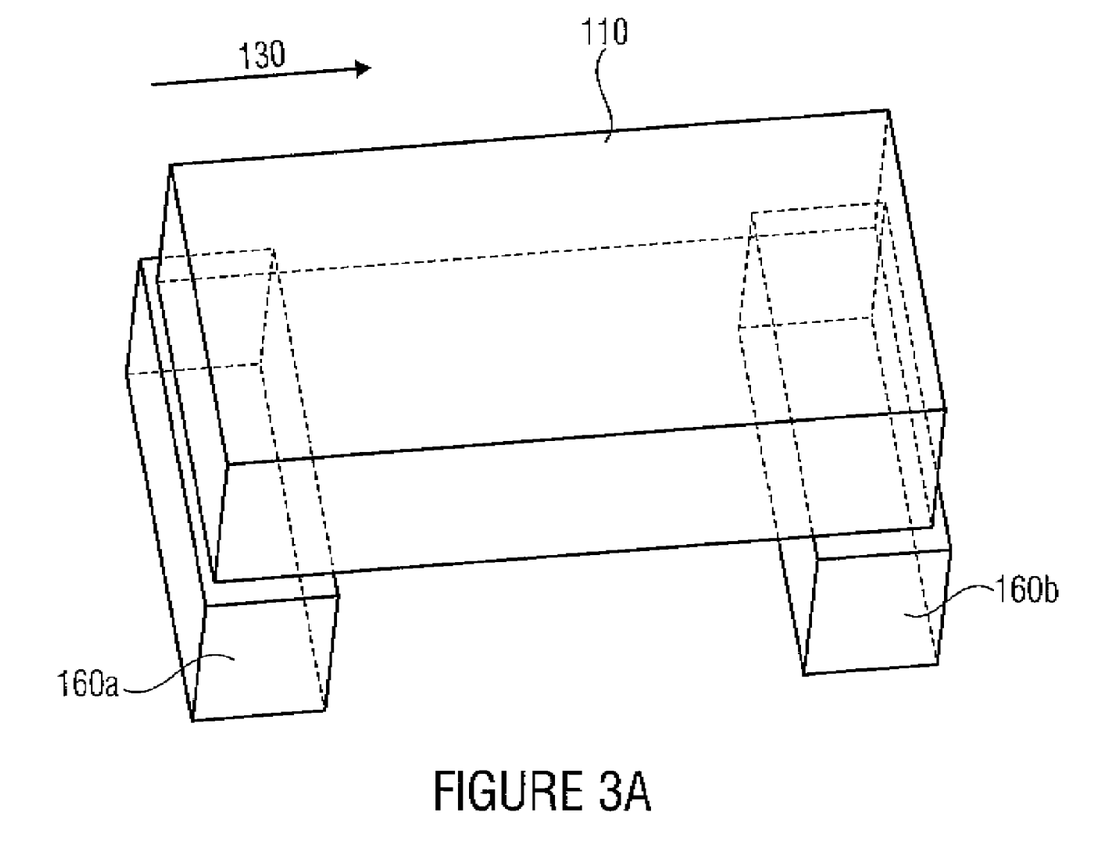
FIG. 3a shows a spatial view of the waveguide with support elements.
Figure 3B:
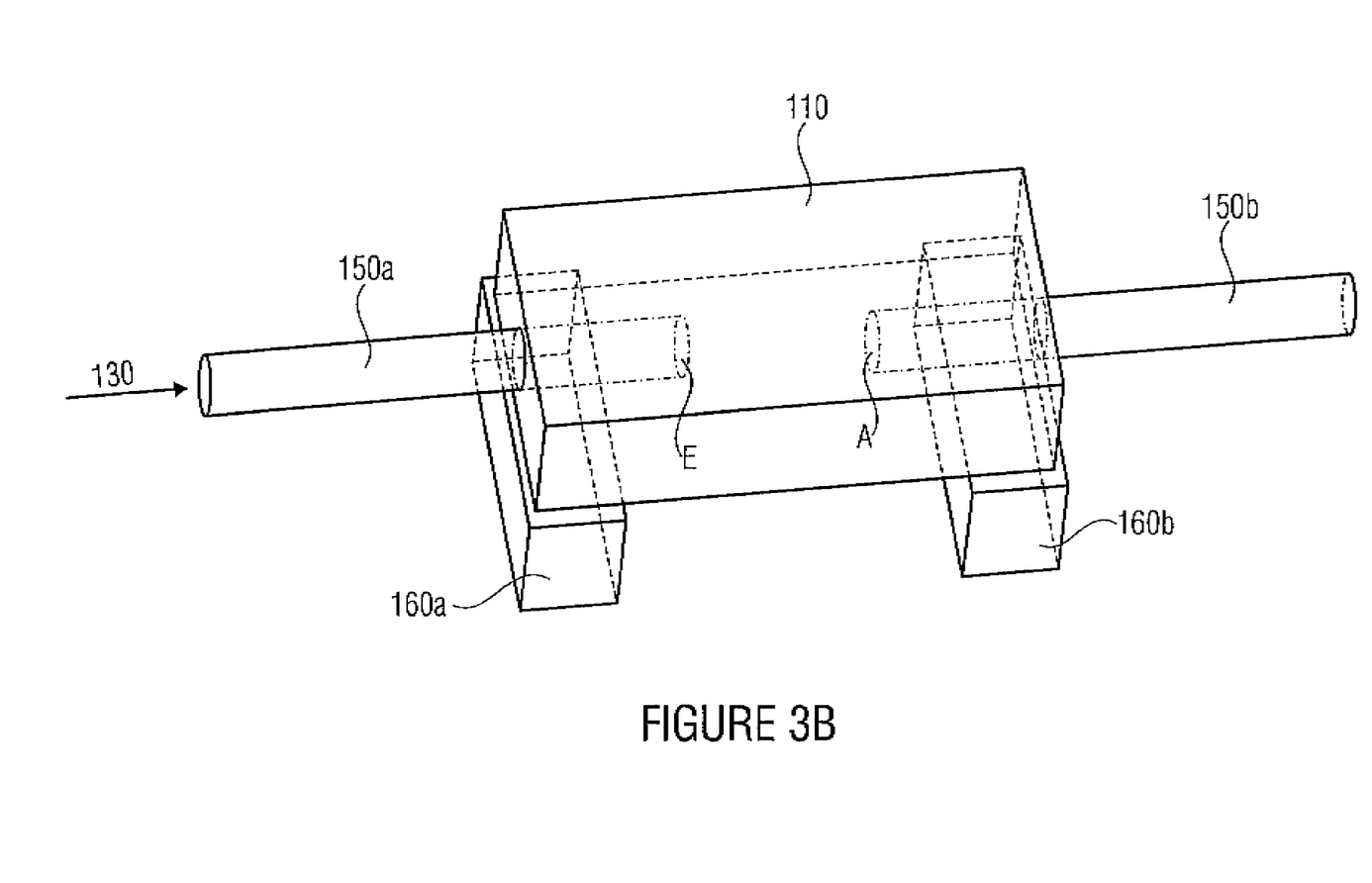
FIG. 3b shows a spatial view of the waveguide with support elements and fiber-optic cables.

FIGS. 3a and 3b show further spatial views of the waveguide 110. FIG. 3a shows the waveguide 110 secured by means of a support 160. The support 160 has a first part 160a and a second part 160b, each disposed on both ends along the wave propagation direction 130, for example. It is advantageous that the contact surface between the support 160 and the waveguide 110 be kept to a minimum, as the contact surface acts as an aperture for the electromagnetic radiation introduced into the waveguide 110.

FIG. 3b shows a spatial view of the waveguide 110 and the support 160 having the first and second parts 160a and 160b, wherein electromagnetic radiation along the wave propagation direction 130 may be coupled into the waveguide 110 by a fiber-optic cable 150. In the embodiment shown in FIG. 3b, the electromagnetic radiation is introduced into the waveguide 110 by means of a first fiber-optic cable 150a, and an optical signal may be coupled out of the waveguide 110 by means of a further fiber-optic cable 150b. As the contact surface of the support 160 relative to the waveguide 110 acts as an aperture for the electromagnetic radiation (or light) entering (at least when the refractive index of the support 160 is larger than the refractive index of the waveguide 110), it is reasonable that the electromagnetic radiation be first introduced, by means of the fiber-optic cable 150a, into the waveguide 110 in a region E which, seen in the wave propagation direction 130, is behind the contact surface between the first part of the support 160a and the waveguide 110. This serves to ensure that the contact area between the first part of the support 160a and the waveguide 110 may not be directly illuminated by the fiber-optic cable 150a and that it is by scattering at the most that light may leave the waveguide 110 at this location. It is also reasonable that the light signal propagating in the waveguide 110 be coupled out of the waveguide 110 by means of the further fiber-optic cable 150b in an output region A before reaching the contact area between the second part of the support 160b and the waveguide 110. This serves to ensure that, between the input region E and the output region A, the propagation of the optical signal from the fiber-optic cable 150a to the further fiber-optic cable 150b is effected along the waveguide 110 without the optical signal being able to leave the waveguide 110 in the intermediate area, for example via a contact to the support 160, thereby, due to total reflection, remaining in the waveguide 110.

Figure 3C:
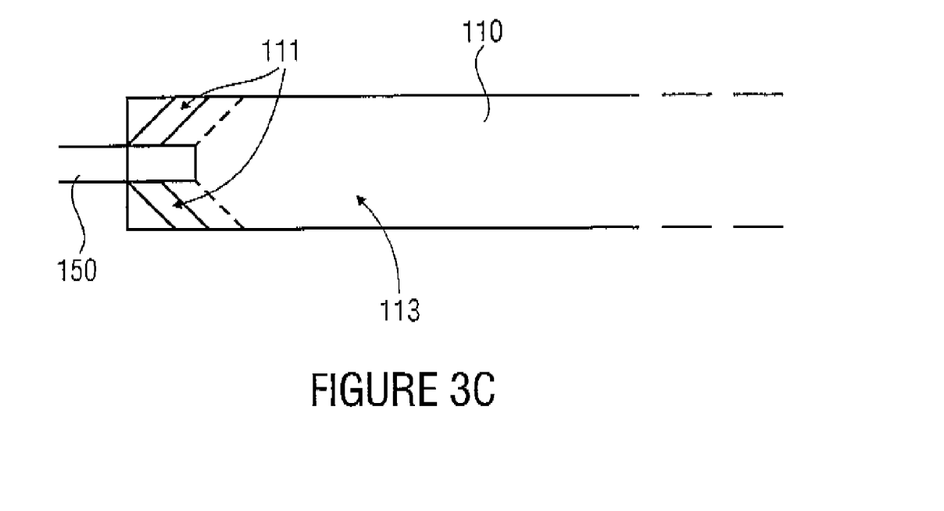
FIG. 3c shows a cross-sectional view for illustrating a part of the waveguide directly illuminatable by a fiber-optic cable.

FIG. 3c shows a cross-sectional view of the waveguide 110 and an optional fiber-optic cable 150, wherein the fiber-optic cable 150 protrudes into the waveguide 110, so that a directly illuminatable part 113 of the waveguide 110 may be illuminated by light having passed through the waveguide 110. Outside the directly illuminatable part 113, a shadow region 111 is formed, which cannot be reached by light unless by back-scattering or reflection. The supports 160 are advantageously arranged towards this shadow area 111. The fiber-optic cable 150 shown here may be both the input-side fiber-optic cable 150a or the further fiber-optic cable 150b.

Figure 4:
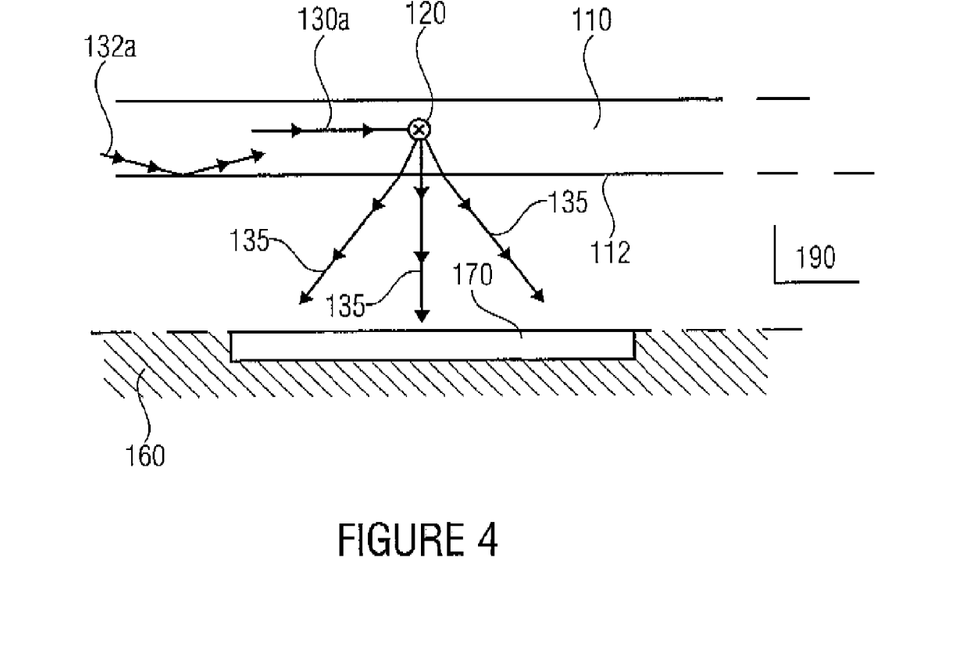
FIG. 4 shows a cross-sectional view of the waveguide and of a photodetector arranged in a position perpendicular to the propagation direction.

FIG. 4 shows an embodiment of a waveguide 110 further comprising a photodetector 170, wherein the photodetector 170 is arranged in a position perpendicular to the propagation direction 130 and offset relative to the waveguide 110. The photodetector 170 may, for example, be fixed by the same support 160 that also fixes the waveguide 110 as shown in FIG. 3.

A light signal 130a interacting with a receptor molecule 120 propagates along the waveguide 110. The receptor molecule 120 may, for example, interact with an analyte molecule or may be chemically connected thereto. As a result of the interaction of the incident light beam 130a with the receptor molecule 120, fluorescence may be effected, for example, which causes the receptor molecule 120 to act as a source for a fluorescent radiation 135. The fluorescent radiation 135 propagates in all directions and in particular in a manner perpendicular to the surface 112 of the waveguide 110. This provides the possibility that the fluorescent light—in contrast to the light 130, 132 propagating in the waveguide 110—can leave the waveguide 110. A refraction along the surface 112 may occur, will however not prevent the fluorescent radiation 135 leaving the waveguide 110 and being able to propagate in the direction of the detector 170, where it may be detected via photodetectors (photodiodes, photothyristors, etc.), for example. As the fluorescence radiation 135 is substantially less in intensity compared to the radiation 130 propagating in the waveguide 110, it is advantageous, as it is the case in the embodiments of the present invention, that the waveguide 110 comprise such a material that the light signals 130, 132 propagating in the waveguide 110 remain in the waveguide 110 as a result of the total reflection on the edge 112 and only the fluorescent light 135 can leave the waveguide 110.

Between the waveguide 110 and the detector 170 the medium 200 may be located, for example, but there may also be formed a gap 190, for example from air, as long as it is ensured that the gap 190 between the waveguide 110 and the detector 170 exhibit a refractive index smaller than the refractive index of the waveguide 110.

Figure 5:
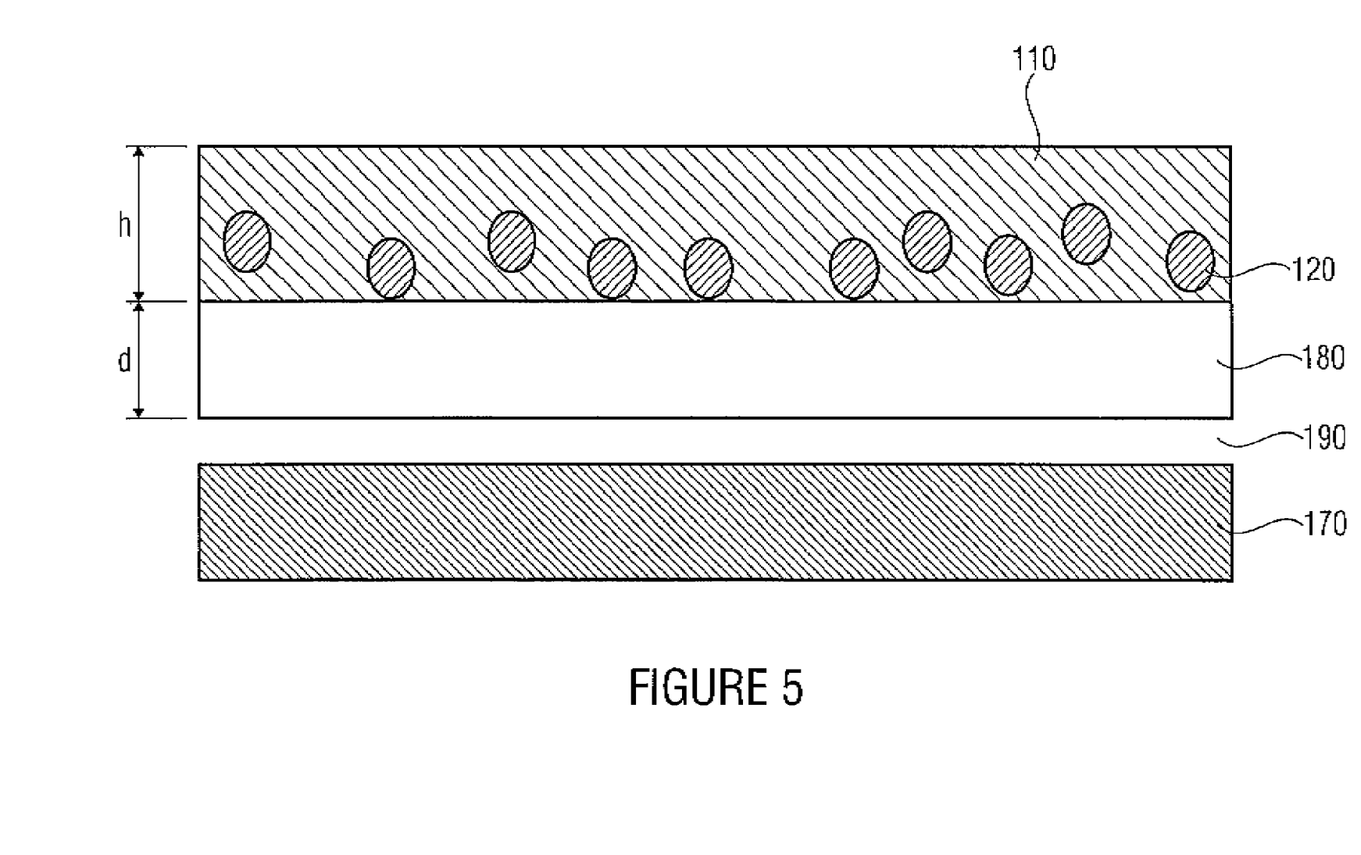
FIG. 5 shows a cross-sectional view of a waveguide according to a further embodiment of the present invention.

FIG. 5 shows a further embodiment, wherein the waveguide 110 is disposed in the form of a layer on a transparent support 180 and the waveguide 110 serves as an immobilization matrix for the receptor molecules 120. As the receptor molecules 120, proteins may be used, for example, which bind glucose so that a glucose sensor chamber may be produced, wherein hydrogel serves as a medium in which the light may propagate. In the embodiment shown in FIG. 5, the support 180 may comprise a glass or silicate substrate, for example, and, to prevent the light signal from leaving the waveguide 110 and the support 180, again a gap 190 may be formed between the support 180 and the photodetector 170, wherein the gap 190 is advantageously filled with a medium having a smaller refractive index than the refractive index of the support 180 (whereby a total reflection on the respective transition surface is again achievable).

In the embodiment shown in FIG. 5, the propagation direction of the light signal may be effected, for example, from left to right or even in a manner perpendicular to the plane of projection. Again, the photodetector 170 is arranged in a manner perpendicular to the propagation direction 130 of the light signal, so that the photodetector 170 is particularly sensitive to fluorescent light and/or any other light propagating perpendicularly to the propagation direction 130 of the light signal.

The embodiment shown in FIG. 5 therefore offers the opportunity to position the photodetector 170 such that it is suitable for analyzing scattered and fluorescent light in particular. As only a very small portion of the exemplary fluorescent light is guided in the hydrogel, this is the advantageous assembly for measuring fluorescence and/or FRET. The detection of the exemplary fluorescent light is effected in a manner perpendicular to the optical train of the light in the waveguide 110, for example. An analog arrangement of the photodetector 170 is also possible for the waveguide 110 shown in FIGS. 3a and 3b. Here, the support 180 should be chosen as thin as possible and advantageously have a thickness d less than 500 μm or less than 200 μm or ranging from 5 μm to 100 μm. The hydrogel layer of the waveguide 110 may, for example, exhibit a height h ranging from 5 μm to 5000 μm or from 10 μm to 1000 μm.

In the arrangement of the photodetector 170, it is of no importance whether the photodetector 170 is disposed above, below or right or left of the hydrogel waveguide 110. For a measurement job (such as of the transmission) it may, however, be advantageous to also dispose a further photodetector at the end of the hydrogel waveguide 110. It is then inserted in place of the further fiber-optic cable 150b in FIG. 3b.

In further embodiments, back-scattering measurements may also be performed, wherein the fiber-optic cable 150a in FIG. 3b may be used for collecting fluorescent light or scattered light, for example, which is then forwarded to a detector. Here, the fiber-optic cable 150a may comprise several fibers, for example, wherein a first part of the fibers serves for feeding light and a second part of the fibers serves for capturing the scattered light.

Figure 6:
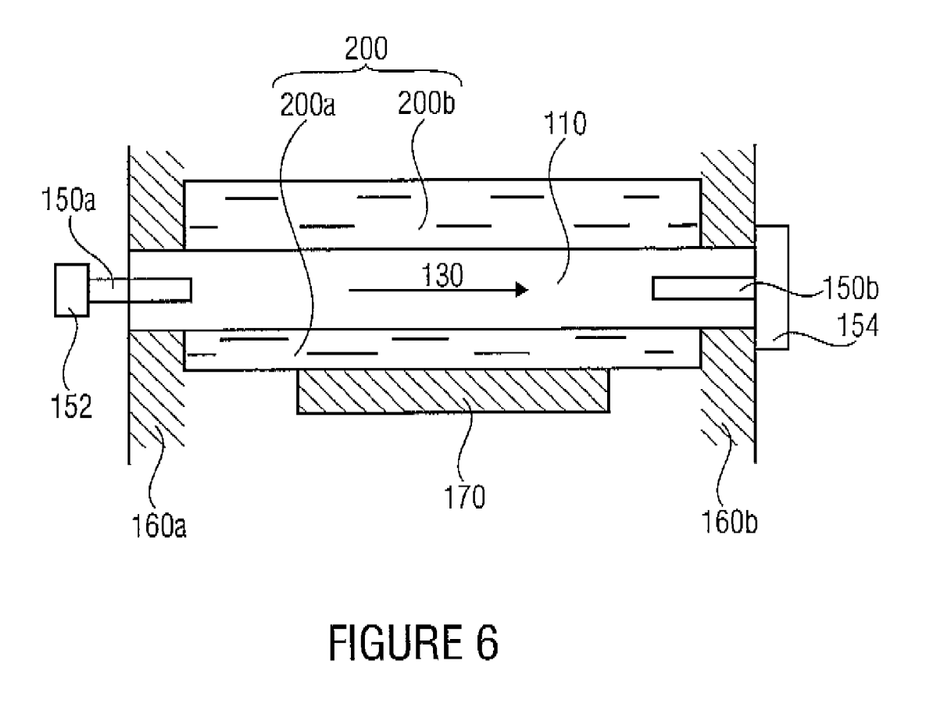
FIG. 6 shows a cross-sectional view of a biosensor having an inventive waveguide.

FIG. 6 shows an embodiment for a biosensor comprising a waveguide 110 being in contact with the medium 200, the waveguide 110 optically connected to a light source 152 (e.g. a laser) via a fiber-optic cable 150a, and the waveguide 110 further being optically connected to means 154 for detecting a light signal (further photodetector) via a further fiber-optic cable 150b. In addition, the biosensor comprises a support 160, which for one thing fixes the waveguide 110 and may optionally form a container into which the medium 200 can be introduced and in addition fixes the photodetector 170. In the embodiment in FIG. 6, the photodetector 170 is again arranged in a manner perpendicular to the propagation direction of the light signal 130, so that the photodetector 170 may in particular detect light in the waveguide 110 produced by fluorescence. Furthermore, the further photodetector 154 may measure the light signal 130, whereby, in particular, possible absorption as a result of the analyte concentration or missing absorption as a result of the analyte concentration in the medium 200 may be ascertained.

The medium 200 may be disposed on both sides of the waveguide 110, for example, so that, as can be seen in the cross-sectional view of FIG. 6, the medium comprises a first proportion 200a and a second proportion 200b. In further embodiments, the waveguide may also be arranged on a side wall or on a bottom or cover of the container so that the waveguide 110 contacts the medium 200 with one side face only. The first or second proportions 200a, 200b may therefore be omitted or be replaced by a gap. It is also possible that the medium 200 propagates along a channel or microchannel and that the waveguide 110 is arranged in a manner perpendicular to the direction of flow of the microchannel or forms an edge region of the microchannel.

In further embodiments, it is also possible that the biosensor is directly implanted so that no separate container for the medium 200 is necessitated and only direct contact to the body fluid to be examined (such as the intercellular serum) is ensured. This may, for example, be used for guaranteeing constant monitoring of a glucose value.

The hydrogel may comprise silicate or polyacrylamide or alginate, for example. The biological receptors or receptor molecules 120 as well as fluorescent substances that may be necessitated are also introduced in the gel synthesis (i.e. in the fabrication of the hydrogel). The hydrogel may be brought into any shape, so that a cuboid or cylindrical shapes are available for applications. The sizes of the gels may vary from 10 μm to 20 mm or from 50 μm to 10 mm or from 500 μm to 5 mm in height (and/or diameter) and from 1 mm to 100 mm or from 5 to 50 mm in length or width. After the synthesis, the fiber-optic cables 150 may be inserted into these gel pieces. The excitation light for the fluorescent substances may be coupled in via the fiber-optic cables 150, for example. The entire assembly may then be kept in a liquid 200 containing the analyte. The analyte diffuses into the gel and there reacts with the immobilizing substances (receptor molecules). The chemical-reaction-specific fluorescent light is accommodated at 90° relative to the excitation light.

Other coupling methods are also conceivable for coupling the glass fiber to the waveguide. For example, the glass fiber may be set upon the input side or have a small distance (<1 mm) to the input side. In addition, coupling by means of beam shaping, i.e. by means of a (micro) lens arranged at a certain distance from the input side, is also possible. When a laser is used as a light source (low beam divergence) the use of fibers or lenses may possibly be completely done away with.

In further embodiments, a further fiber-optic cable 150b may be inserted into the gel (hydrogel) so that the further fiber-optic cable 150b may also be coupled to a further photodetector 154 and therefore receive a sensor signal.

Dimensions of the cross-section of the waveguide 110 or the waveguide core are typically in the order of 10 μm to several mm, the length of the hydrogel waveguide 110 advantageously ranges from 1 mm to several cm.

Therefore, embodiments of the present invention describe an optical biosensor enabling a coupling efficiency between the receptor molecules 120 and the transducer or the waveguide 110 that goes substantially beyond a conventional solution.

Embodiments therefore also in particular comprise an optical waveguide, the core material of which comprises a hydrogel, which serves as an immobilization matrix having receptor molecules embedded therein. The waveguide property specifically enables that—in contrast to conventional methods—a maximum number of receptor molecules are available for the detection.

As a light source, blue light in the spectral range between approximately 400 and approximately 440 nm may be used, for which blue laser diodes may be utilized, for example. Diodes are advantageous as they can be fabricated in minute sizes and in addition to that are very energy-efficient. This is of major importance in particular for implantable biosensors.

The implanted biosensors may further optionally comprise a wireless interface so that data (e.g. glucose concentration) may be transmitted to an external evaluation unit. For example, the external evaluation unit may comprise a mobile telephone, PDA or the like, and may in addition (optionally) forward the data to a physician. This enables permanent monitoring of the exemplary glucose concentration. Optionally, the biosensor may also be coupled to means for injecting medicine, so that automatic (medicinal) measures may be taken in case a threshold value is exceeded. In further embodiments, however, other concentrations may also be automatically monitored, the glucose concentration just being one example. For such medical applications it is of particular advantage that hydrogels are very well tolerated biologically.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A waveguide core made of hydrogel comprising receptor molecules, such that the hydrogel serves as an immobilization matrix for the receptor molecules embedded therein, wherein
   the waveguide core is arranged to guide light by utilizing total internal reflection; and
   at least a part of the hydrogel is adapted to free-float within a surrounding medium having a refractive index that is lower than that of the hydrogel.

2. The waveguide core of claim 1, which exhibits a length and a cross-section, the cross-section exhibiting a smallest extension at least three times smaller than the length.

3. The waveguide core of claim 2, wherein the cross-section exhibits a largest extension and a smallest extension, the largest extension and the smallest extension ranging from 10 μm to 20 mm or from 50 μm to 10 mm or from 0.5 mm to 5 mm.

4. The waveguide core of claim 2, wherein the length of the waveguide ranges from 1 mm to 100 mm or from 5 mm to 50 mm.

5. The waveguide core of claim 1, further comprising a transparent support, wherein the hydrogel is disposed on a main surface of the transparent support.

6. The waveguide core of claim 5, wherein the support comprises a thickness perpendicular to the main surface and the thickness ranges from 1 µm to 500 µm or from 5 µm to 100 µm.

7. The waveguide core of claim 5, wherein the hydrogel is implemented as a layer on the transparent support and the layer comprises a layer thickness ranging from 10 µm to 1000 µm.

8. The waveguide core of claim 2, wherein the cross-section of the waveguide core exhibits a square or a rectangular or a round shape.

9. The waveguide core of claim 1, wherein the hydrogel comprises a silicate or a polyacrylamide or an alginate.

10. A waveguide assembly, comprising:
   a waveguide core made of hydrogel comprising receptor molecules, such that the hydrogel serves as an immobilization matrix for the receptor molecules embedded therein, wherein the waveguide core includes an input side and is arranged to guide light by utilizing total internal reflection; and
   a fiber-optic cable; wherein
   the fiber-optic cable protrudes into the input side of the waveguide core or is set upon the input side or is optically coupled to the input side via a lens; and
   at least a part of the hydrogel is adapted to free-float within a surrounding medium having a refractive index that is lower than that of the hydrogel.

11. The waveguide assembly of claim 10, wherein the waveguide core comprises a part directly illuminatable by the fiber-optic cable and a support, the support being arranged outside the directly illuminatable part.

12. The waveguide assembly of claim 10, further comprising a further fiber-optic cable, the further fiber-optic cable protruding into the hydrogel or being set upon the hydrogel or being optically coupled to the hydrogel via a lens so that the fiber-optic cable and the further fiber-optic cable are optically coupled via the hydrogel.

13. The waveguide assembly of claim 10, further comprising a photodetector, and the photodetector being arranged to detect electromagnetic radiation guided by the waveguide assembly or leaving the waveguide assembly laterally through an edge.

14. A waveguide, comprising:
   a waveguide core made of hydrogel comprising receptor molecules, such that the hydrogel serves as an immobilization matrix for the receptor molecules embedded therein, wherein
   the waveguide core is arranged to guide light by utilizing total internal reflection;
   a waveguide cladding, the waveguide cladding exhibiting a refractive index smaller than a refractive index of the waveguide core; and
   the waveguide cladding comprises a further hydrogel.

15. An optical sensor, comprising:
   a waveguide core made of hydrogel comprising receptor molecules, such that the hydrogel serves as an immobilization matrix for the receptor molecules embedded therein, wherein
   the waveguide core is arranged to guide light by utilizing total internal reflection;
   a detector arranged to detect electromagnetic radiation leaving the waveguide core; and
   at least a part of the hydrogel is adapted to free-float within a surrounding medium having a refractive index that is lower than that of the hydrogel.

16. The optical sensor of claim 15, further comprising a coupler arranged to couple electromagnetic radiation into the waveguide core.

17. The optical sensor of claim 15, further comprising a container arranged to receive a medium so that the medium contacts the waveguide core and the hydrogel is configured to exhibit a refractive index larger than a refractive index of the medium in the container.

18. The optical sensor of claim 15, wherein the detector is configured such that radiation leaving the waveguide core or the waveguide assembly or the waveguide laterally through an edge is detectable.

19. The optical sensor of claim 15, wherein the detector is configured to detect a fluorescent light produced in the hydrogel on contact to a medium.

20. The optical sensor of claim 15, further comprising an evaluation unit, and the evaluation unit being configured to ascertain, from electromagnetic radiation determined by the detector, an analyte concentration in a medium in contact with the waveguide core.

21. The optical sensor of claim 20, wherein the receptor molecules are configured to bind glucose so that a glucose concentration in the medium is determinable.

22. A waveguide core according to claim 5, wherein a refractive index of the hydrogel is lower than a refractive index of the transparent support.

23. A waveguide core according to claim 2, wherein the cross-section of the waveguide core exhibits a square or a rectangular or a polygonic shape.

24. A waveguide core according to claim 10, further comprising a photodetector, the photodetector being arranged to detect electromagnetic radiation leaving the waveguide assembly laterally through a long side of the waveguide core.

* * * * *